United States Patent
Voth et al.

(10) Patent No.: US 10,238,308 B2
(45) Date of Patent: Mar. 26, 2019

(54) METHODS AND SYSTEMS FOR GENERATING ELECTROPHYSIOLOGICAL MAPS

(71) Applicant: St. Jude Medical, Cardiology Division, Inc., St. Paul, MN (US)

(72) Inventors: Eric J. Voth, Maplewood, MN (US); Cable Patrick Thompson, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 126 days.

(21) Appl. No.: 15/279,558

(22) Filed: Sep. 29, 2016

(65) Prior Publication Data

US 2017/0095172 A1 Apr. 6, 2017

Related U.S. Application Data

(60) Provisional application No. 62/237,897, filed on Oct. 6, 2015.

(51) Int. Cl.
*G06K 9/36* (2006.01)
*A61B 5/044* (2006.01)
(Continued)

(52) U.S. Cl.
CPC .............. *A61B 5/044* (2013.01); *A61B 5/042* (2013.01); *A61B 5/04012* (2013.01);
(Continued)

(58) Field of Classification Search
CPC ..... A61B 5/044; A61B 5/0444; A61B 5/0448; A61B 5/0452; A61B 5/04012;
(Continued)

(56) References Cited

U.S. PATENT DOCUMENTS 6,233,476 B1    5/2001   Strommer et al.
6,498,944 B1   12/2002   Ben-Haim et al.
(Continued)

FOREIGN PATENT DOCUMENTS

WO        2012092016 A1      7/2012

OTHER PUBLICATIONS

Adams et al, "Adaptively Sampled Particle Fluids," ACM Transactions on Graphics, 26, 3 (Proceedings of ACM SIGGRAPH 2007), Aug. 5, 2007, p. 48:1-48:7.
(Continued)

*Primary Examiner* — Dwayne D Bost
*Assistant Examiner* — Stephen M Brinich
(74) *Attorney, Agent, or Firm* — Armstrong Teasdale LLP

(57) ABSTRACT

The present disclosure provides systems and methods for generating an electrophysiological map of a geometric structure. The system includes a computer-based model construction system configured to acquire electrical information at a plurality of diagnostic landmark points, assign a color value, based on the acquired electrical information, to each of the diagnostic landmark points, create a first 3D texture region storing floats for a weighted physiological metric, create a second 3D texture region storing floats for a total weight, for each diagnostic landmark point, additively blend the color value of the diagnostic landmark point into voxels of the first 3D texture region that are within a predetermined distance, normalize the colored voxels using the second 3D texture region to generate a normalized 3D texture map, generate the electrophysiological map from the normalized 3D texture map and a surface of the geometric structure, and display the generated electrophysiological map.

20 Claims, 9 Drawing Sheets

(51) Int. Cl.
*A61B 5/04* (2006.01)
*A61B 5/042* (2006.01)
*A61B 5/0432* (2006.01)
*G06T 15/04* (2011.01)
*G06T 15/08* (2011.01)
*G06T 19/20* (2011.01)
*G06T 15/50* (2011.01)
*A61B 34/10* (2016.01)
*A61B 34/20* (2016.01)

(52) U.S. Cl.
CPC ............ *A61B 5/0432* (2013.01); *G06T 15/04* (2013.01); *G06T 15/08* (2013.01); *G06T 15/503* (2013.01); *G06T 19/20* (2013.01); *A61B 2034/104* (2016.02); *A61B 2034/105* (2016.02); *A61B 2034/2072* (2016.02); *G06T 2210/41* (2013.01); *G06T 2219/2012* (2013.01)

(58) Field of Classification Search
CPC . A61B 5/04014; A61B 5/04017; A61B 5/042; A61B 5/0424; A61B 5/0432; A61B 5/0436; G06T 11/008; G06T 15/04; G06T 15/06; G06T 15/08; G06T 15/10; G06T 15/503; G06T 19/20; G06T 19/00; G06T 19/003; G06T 19/205
USPC ......... 382/154, 285, 108, 276; 345/419–420, 345/424, 427–428; 600/424, 410
See application file for complete search history.

(56) References Cited

U.S. PATENT DOCUMENTS

| | | | |
|---|---|---|---|
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 8,103,073 B2* | 1/2012 | Hundley | A61B 5/055 128/920 |
| 8,638,328 B2 | 1/2014 | Lin | |
| 2006/0110017 A1* | 5/2006 | Tsai | G06T 7/0012 382/128 |
| 2012/0087564 A1* | 4/2012 | Tsujita | A61B 8/0808 382/131 |
| 2016/0292912 A1* | 10/2016 | Sebok | G06F 3/04815 |

OTHER PUBLICATIONS

Yilmaz et al, "Usage of spline interpolation in catheter-based cardiac mapping", Turkish Journal of Electrical Engineering and Computer Sciences, Jan. 1, 2010, p. 989-1002, http://journals.tubitak.gov.tr/elektrik/issues/elk-10-18-9/elk-18-6-5-0991-277.pdf.

Chinchapatnam et al, "Voxel Based Adaptive Meshless Method of Cardiac Electrophysiology Simulation", Jun. 3, 2009, Functional Imaging and Modeling of the Heart, p. 189-190.

* cited by examiner

METHODS AND SYSTEMS FOR GENERATING ELECTROPHYSIOLOGICAL MAPS

CROSS-REFERENCE TO RELATED APPLICATIONS

This application claims the benefit of priority to U.S. Provisional Patent Application No. 62/237,897 filed on Oct. 6, 2015, entitled "METHODS AND SYSTEMS FOR GENERATING ELECTROPHYSIOLOGICAL MAPS," the entire contents and disclosure of which are hereby incorporated herein by reference in their entirety.

FIELD OF THE DISCLOSURE

This disclosure relates to systems and methods for generating an electrophysiological map of a geometric structure. More particularly, this disclosure relates to computer-implemented systems and methods for generating an electrophysiological map of a geometric structure, such as, for example, an intra-cardiac structure.

BACKGROUND

It is known that various computer-based systems and computer-implemented methodologies can be used to generate multi-dimensional surface models of geometric structures, such as, for example, anatomic structures. More specifically, a variety of systems and methods have been used to generate multi-dimensional surface models of the heart and/or particular portions thereof.

At least some known algorithms for interpolating and rendering contact maps are heuristic. However, such algorithms may generate incomplete and suboptimal triangulations when an average distance between diagnostic landmark (DxL) points is near or below an average distance between geometry points (i.e., vertices). Notably, DxL maps may have regions that look substantially different based on a facet size setting, the order of point collection, and/or an interpolation slider setting. Further, such algorithms may also become computationally expensive when large numbers (e.g., thousands) of DxL points are collected.

BRIEF SUMMARY OF THE DISCLOSURE

In one embodiment, the present disclosure is directed to a system for generating an electrophysiological map of a geometric structure. The system includes a computer-based model construction system configured to be coupled to a device that includes at least one sensor configured to acquire a set of original location data points corresponding to respective locations on a surface of the geometric structure. The computer-based model construction system is further configured to acquire electrical information at a plurality of diagnostic landmark points, assign a color value, based on the acquired electrical information, to each of the diagnostic landmark points, create a first three-dimensional (3D) texture region storing floats for a weighted physiological metric, create a second 3D texture region storing floats for a total weight, for each diagnostic landmark point, additively blend the color value of the diagnostic landmark point into voxels of the first 3D texture region that are within a predetermined distance from the diagnostic landmark point, normalize the colored voxels using the second 3D texture region to generate a normalized 3D texture map, generate the electrophysiological map from the normalized 3D texture map and the surface of the geometric structure, and display the generated electrophysiological map.

In another embodiment, the present disclosure is directed to a computer-implemented method of generating an electrophysiological map of a geometric structure. The method includes receiving a set of original location data points corresponding to respective locations on a surface of the geometric structure, generating a reference surface based on the received original location data points, acquiring electrical information at a plurality of diagnostic landmark points, assigning a color value, based on the acquired electrical information, to each of the diagnostic landmark points, creating a first three-dimensional (3D) texture region storing floats for a weighted physiological metric, creating a second 3D texture region storing floats for a total weight, for each diagnostic landmark point, additively blending the color value of the diagnostic landmark point into voxels of the first 3D texture region that are within a predetermined distance from the diagnostic landmark point, normalizing the colored voxels using the second 3D texture region to generate a normalized 3D texture map, generating the electrophysiological map from the normalized 3D texture map and the surface of the geometric structure, and displaying the generated electrophysiological map.

In another embodiment, the present disclosure is directed to a processing apparatus for generating an electrophysiological map of a geometric structure. The processing apparatus is configured to receive a set of original location data points corresponding to respective locations on a surface of the geometric structure, generate a reference surface based on the received original location data points, acquire electrical information at a plurality of diagnostic landmark points, assign a color value, based on the acquired electrical information, to each of the diagnostic landmark points, create a first three-dimensional (3D) texture region storing floats for a weighted physiological metric, create a second 3D texture region storing floats for a total weight, for each diagnostic landmark point, additively blend the color value of the diagnostic landmark point into voxels of the first 3D texture region that are within a predetermined distance from the diagnostic landmark point, normalize the colored voxels using the second 3D texture region to generate a normalized 3D texture map, generate the electrophysiological map from the normalized 3D texture map and the surface of the geometric structure, and display the generated electrophysiological map.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for generating an electrophysiological map (e.g., of an interior surface of the heart). The electrophysiological map is generated using a kernel-evaluation loop that fills a large three-dimensional texture map, normalizes color indices, and renders the electrophysiological map directly or indirectly from the three-dimensional texture map, as described herein. This prevents interpolation problems, allows much more electrophysiological detail to be mapped even with geometries including large facets, and runs more quickly that at least some known algorithms.

Figure 1:
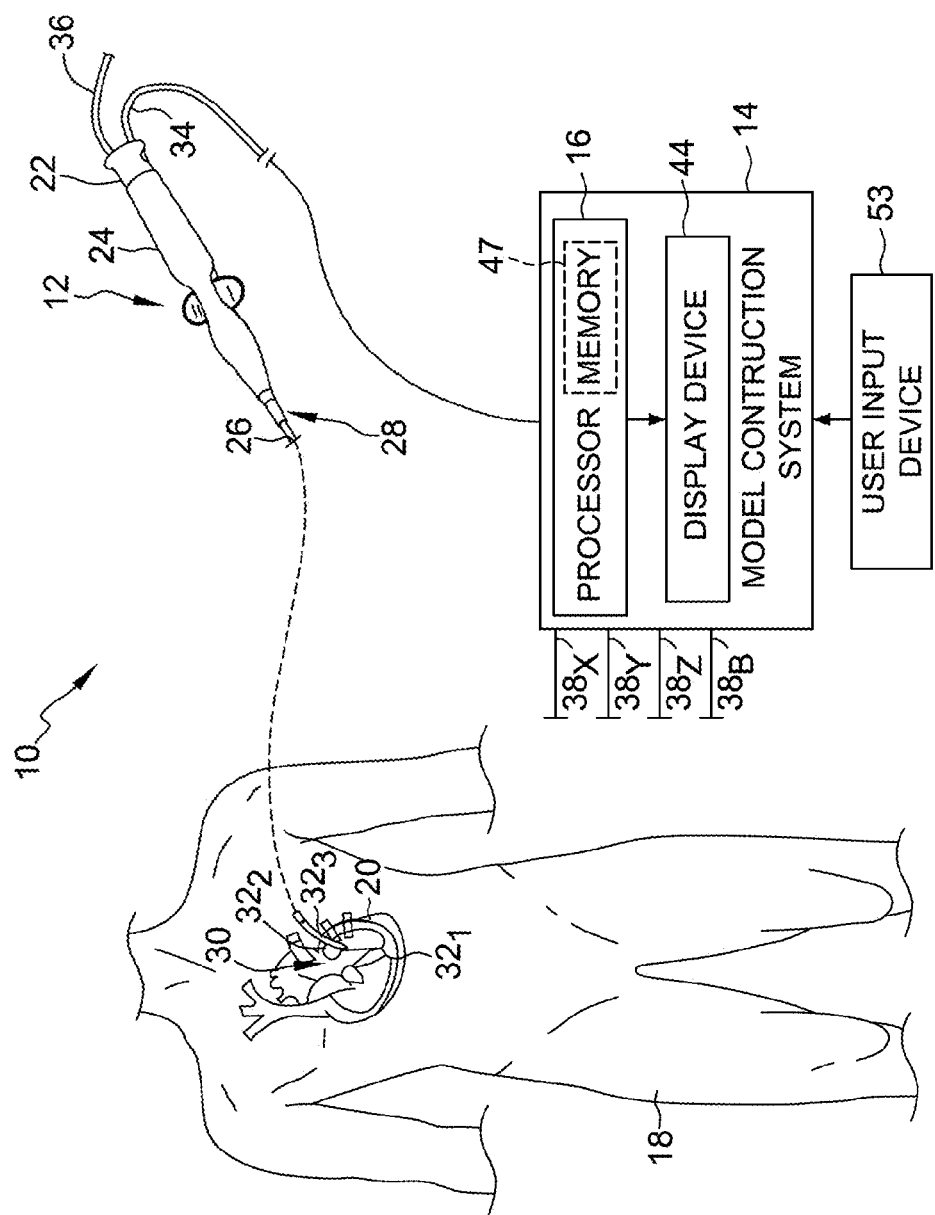
FIG. 1 is a diagrammatic view of a system for generating a multi-dimensional surface model of a geometric structure according to one embodiment.

Referring now to the drawings wherein like reference numerals are used to identify identical components in the various views, FIG. 1 illustrates one exemplary embodiment of a system 10 for generating a multi-dimensional surface model of one or more geometric structures. As will be described below, in this embodiment, the model generated by system 10 is a three-dimensional model. It will be appreciated, however, that while the generation of a three-dimensional model is described below, the present disclosure is not meant to be so limited. Rather, in other embodiments, system 10 may be configured to generate multi-dimensional models other than in three dimensions, and such embodiments remain within the spirit and scope of the present disclosure.

It should be further noted that while the following description focuses primarily on the use of system 10 in the generation of models of anatomic structures, and cardiac structures in particular, the present disclosure is not meant to be so limited. Rather, system 10, and the methods and techniques used thereby, may be applied to the generation of three-dimensional models of any number of geometric structures, including anatomic structures other than cardiac structures. However, for purposes of illustration and ease of description, the description below will be focused on the use of system 10 in the generation of three-dimensional models of cardiac structures.

With continued reference to FIG. 1, in this embodiment, the system 10 includes, among other components, a medical device and a model construction system 14. In this embodiment, medical device is a catheter 12, and model construction system 14 includes, in part, a processing apparatus 16. Processing apparatus 16 may take the form of an electronic control unit, for example, that is configured to construct a three-dimensional model of structures within the heart using data collected by catheter 12.

As illustrated in FIG. 1, catheter 12 is configured to be inserted into a patient's body 18, and more particularly, into the patient's heart 20. Catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient), and one or more sensors 32 (e.g., $32_1$, $32_2$, $32_3$) mounted in or on shaft 26 of catheter 12. In this embodiment, sensors 32 are disposed at or near distal end 30 of shaft 26. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Connector 22 provides mechanical, fluid, and electrical connection(s) for cables, such as, for example, cables 34, 36 extending to model construction system 14 and/or other components of system 10 (e.g., a visualization, navigation, and/or mapping system (if separate and distinct from model construction system 14), an ablation generator, irrigation source, etc.). Connector 22 is conventional in the art and is disposed at proximal end 28 of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient. For example, handle 24 may include means to change the length of a steering wire extending through catheter 12 to distal end 30 of shaft 26 to steer shaft 26. Handle 24 is also conventional in the art and it will be understood that the construction of handle 24 may vary. In other embodiments, catheter 12 may be robotically driven or controlled. Accordingly, rather than a clinician manipulating a handle to steer or guide catheter 12 and shaft 26 thereof, in such an embodiments, a robot is used to manipulate catheter 12.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments. Shaft 26 may be made from conventional materials such as polyurethane, and defines one or more lumens configured to house and/or transport electrical conductors, fluids, or surgical tools. Shaft 26 may be introduced into a blood vessel or other structure within the body 18 through a conventional introducer. Shaft 26 may then be steered or guided through body 18 to a desired location, such as heart 20, using means well known in the art.

Sensors 32 mounted in or on shaft 26 of catheter 12 may be provided for a variety of diagnostic and therapeutic purposes including, for example and without limitation, electrophysiological studies, pacing, cardiac mapping, and ablation. In this embodiment, one or more of sensors 32 are provided to perform a location or position sensing function. More particularly, and as will be described in greater detail below, one or more of sensors 32 are configured to be a positioning sensor(s) that provides information relating to the location (position and orientation) of catheter 12, and distal end 30 of shaft 26 thereof, in particular, at certain points in time. Accordingly, as catheter 12 is moved along a surface of a structure of interest of heart 20 and/or about the interior of the structure, sensor(s) 32 can be used to collect location data points that correspond to the surface of, and/or other locations within, the structure of interest. These location data points can then be used by, for example, model construction system 14, in the construction of a three-dimensional model of the structure of interest, which will be described in greater detail below. For purposes of clarity and illustration, the description below will discuss an embodiment wherein multiple sensors 32 of catheter 12 comprise positioning sensors. It will be appreciated, however, that in other embodiments, which remain within the spirit and scope of the present disclosure, catheter 12 may comprise both one or more positioning sensors as well as other sensors configured to perform other diagnostic and/or therapeutic functions.

As briefly described above, and as will be described in greater detail below, model construction system 14 is configured to construct a three-dimensional model of structures within the heart using, in part, location data collected by catheter 12. More particularly, processing apparatus 16 of model construction system 14 is configured to acquire location data points collected by sensor(s) 32 and to then use those location data points in the construction or generation of a model of the structure(s) to which the location data points correspond. In this embodiment, model construction system 14 acquires the location data points by functioning with sensors 32 to collect location data points. In other embodiments, however, model construction system 14 may simply acquire the location data points from sensors 32 or another component in system 10, such as, for example, a memory or other storage device that is part of model construction system 14 or accessible thereby, without affirmatively taking part in the collection of the location data points. Model construction system 14 is configured to construct a three-dimensional model based on some or all of the collected location data points. For purposes of illustration and clarity, the description below will be limited to an embodiment wherein model construction system 14 is configured to both construct the model and also acquire location data points by functioning with sensor(s) 32 in the collection of the location data points. It will be appreciated, however, that other embodiments wherein model construction system 14 only acquires location data points from sensor(s) 32 or another component of system 10 and then constructs a three-dimensional model based thereon remain within the spirit and scope of the present disclosure.

Accordingly, in this embodiment, in addition to constructing a model of a structure, model construction system 14 is configured to function with sensor(s) 32 to collect location data points that are used in the construction of a three-dimensional model. Model construction system 14 may comprise an electric field-based system, such as, for example, the EnSite™ NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, model construction system 14 may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

As briefly described above, sensor(s) 32 of catheter 12 include positioning sensors. Sensor(s) 32 produce signals indicative of catheter location (position and/or orientation) information. In this embodiment, wherein model construction system 14 is an electric field-based system, sensor(s) 32 may comprise one or more electrodes. Alternatively, in an embodiment where model construction system 14 is a magnetic field-based system, sensor(s) 32 may include one or more magnetic sensors configured to detect one or more characteristics of a low-strength magnetic field. For instance, in one exemplary embodiment, sensor(s) 32 may include magnetic coils disposed on or in shaft 26 of catheter 12.

For purposes of clarity and illustration, model construction system 14 will hereinafter be described as including an electric field-based system, such as, for example, the EnSite™ NavX™ system identified above. It will be appreciated that while the description below is primarily limited to an embodiment wherein sensor(s) 32 include one or more electrodes, in other embodiments, sensor(s) 32 may include one or more magnetic field sensors (e.g., coils). Accordingly, model construction systems that include positioning sensor(s) other than the sensors or electrodes described below remain within the spirit and scope of the present disclosure.

Figure 2:
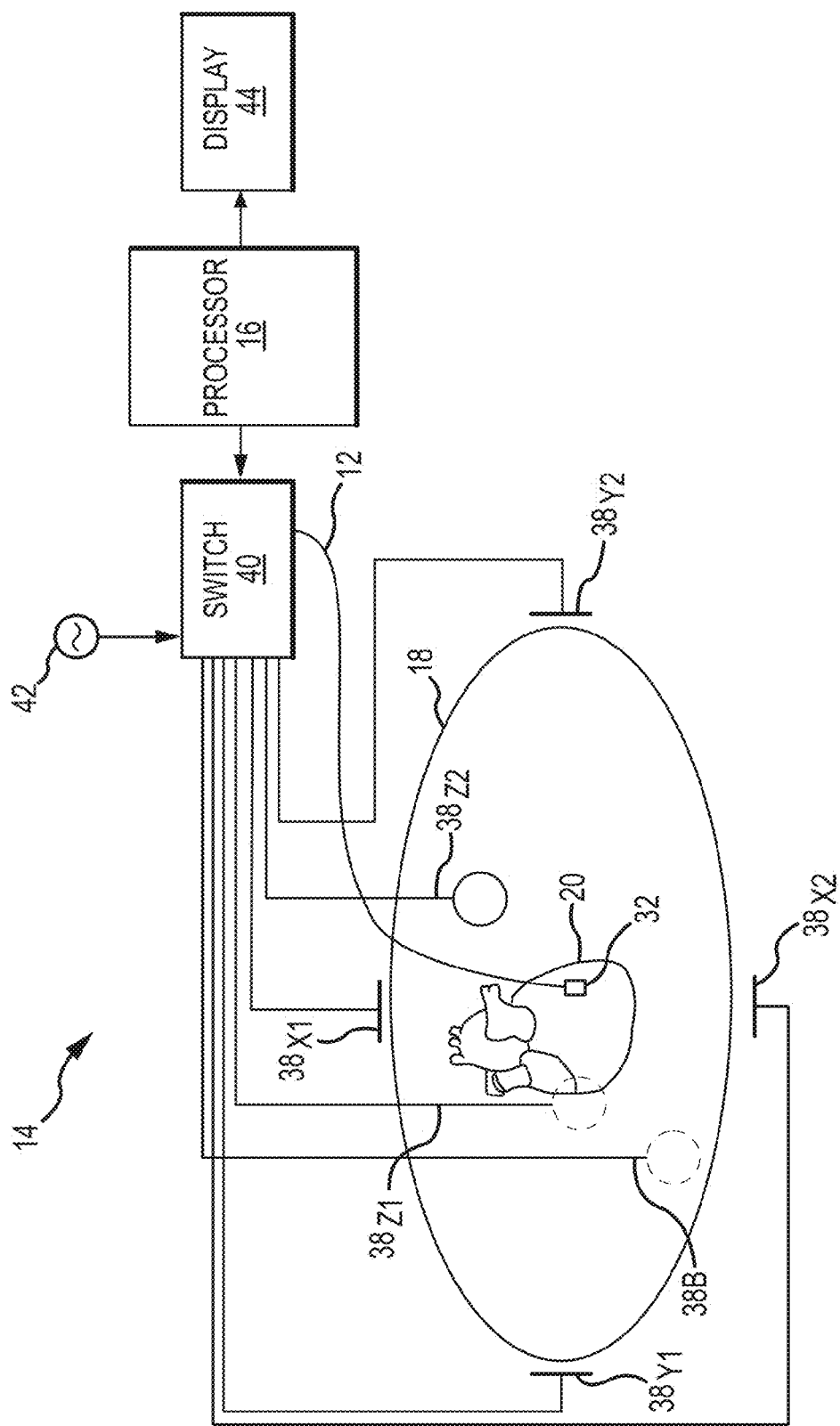
FIG. 2 is a diagrammatic and schematic view of a model construction system of the system illustrated in FIG. 1.

With reference to FIG. 2, in addition to the processing apparatus 16, model construction system 14 may include, among other possible components, a plurality of patch electrodes 38, a multiplex switch 40, a signal generator 42, and a display device 44. In other embodiments, some or all of these components are separate and distinct from model construction system 14 but are electrically connected to, and configured for communication with, model construction system 14.

Processing apparatus 16 may include a programmable microprocessor or microcontroller, or may include an application specific integrated circuit (ASIC). Processing apparatus 16 may include a central processing unit (CPU) and an input/output (I/O) interface through which the processing apparatus 16 may receive a plurality of input signals including, for example, signals generated by patch electrodes 38 and sensor(s) 32, and generate a plurality of output signals including, for example, those used to control and/or provide data to, for example, display device 44 and switch 40. Processing apparatus 16 may be configured to perform various functions, such as those described in greater detail above and below, with appropriate programming instructions or code (i.e., software). Accordingly, processing apparatus 16 is programmed with one or more computer programs encoded on a computer storage medium for performing the functionality described herein.

With the possible exception of patch electrode $38_B$ called a "belly patch," patch electrodes 38 are provided to generate electrical signals used, for example, in determining the position and orientation of catheter 12. In one embodiment, patch electrodes 38 are placed orthogonally on the surface of body 18 and are used to create axes-specific electric fields within body 18. For instance, in one embodiment, patch electrodes $38_{X1}$, $38_{X2}$ may be placed along a first (x) axis.

Patch electrodes $38_{Y1}$, $38_{Y2}$ may be placed along a second (y) axis, and patch electrodes $38_{Z1}$, $38_{Z2}$ may be placed along a third (z) axis. Each of patch electrodes 38 may be coupled to multiplex switch 40. In this embodiment, processing apparatus 16 is configured, through appropriate software, to provide control signals to switch 40 to thereby sequentially couple pairs of electrodes 38 to signal generator 42. Excitation of each pair of electrodes 38 generates an electric field within body 18 and within an area of interest such as heart 20. Voltage levels at non-excited electrodes 38, which are referenced to belly patch $38_B$, are filtered and converted and provided to processing apparatus 16 for use as reference values.

In this embodiment, sensor(s) 32 of catheter 12 are electrically coupled to processing apparatus 16 and are configured to serve a position sensing function. More particularly, sensor(s) 32 are placed within electric fields created in body 18 (e.g., within the heart) by exciting patch electrodes 38. For purposes of clarity and illustration only, the description below will be limited to an embodiment wherein a single sensor 32 is placed within electric fields. It will be appreciated, however, that in other embodiments that remain within the spirit and scope of the present disclosure, a plurality of sensors 32 can be placed within the electric fields and then positions and orientations of each sensor can be determined using the techniques described below.

When disposed within the electric fields, sensor 32 experiences voltages that are dependent on the location between patch electrodes 38 and the position of sensor 32 relative to tissue. Voltage measurement comparisons made between sensor 32 and patch electrodes 38 can be used to determine the location of sensor 32 relative to the tissue. Accordingly, as catheter 12 is swept about or along a particular area or surface of interest, processing apparatus 16 receives signals (location information) from sensor 32 reflecting changes in voltage levels on sensor 32 and from the non-energized patch electrodes 38. Using various known algorithms, the processing apparatus 16 may then determine the location (position and orientation) of sensor 32 and record it as a location data point 46 (also referred to herein as "data point 46" and illustrated in FIG. 3) corresponding to a location of sensor 32, and therefore, a point on the surface or in the interior of the structure of interest being modeled, in a memory or storage device, such as memory 47, associated with or accessible by processing apparatus 16. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Further, locations of other portions of catheter 12 may be inferred from measurements at sensors 32, such as by interpolation or extrapolation, to generate further location data points 46. In any event, the collection of location data points 46 ($46_1$, $46_2$, . . . , $46_n$) taken over time results in the formation of a point cloud 48 (best shown in FIG. 3) stored in the memory or storage device.

While the description above has thus far been generally with respect to an orthogonal arrangement of patch electrodes 38, the present disclosure is not meant to be so limited. Rather, in other embodiments, non-orthogonal arrangements may be used to determine the location coordinates of sensor 32. For example, and in general terms, FIGS. 4A-4D depict a plurality of exemplary non-orthogonal dipoles $D_0$, $D_1$, $D_2$, and $D_3$, set in a coordinate system 50. In FIGS. 4A-4D, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intra-cardiac sensor, such as sensor 32, resulting from a predetermined set of drive (source sink) configurations may be combined algebraically to yield the same effective potential as would be obtained simply by driving a uniform current along the orthogonal axes. Any two of the patch electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., belly patch $38_B$, while the unexcited patch electrodes measure voltage with respect to the ground reference. Sensor 32 placed in heart 20 is also exposed to the field for a current pulse and is measured with respect to ground (e.g., belly patch $38_B$).

In another exemplary embodiment, multiple patch electrodes 38 may be arranged linearly along a common axis. In such an embodiment, excitation of an electrode pair comprising one of patch electrodes 38 and an electrode mounted on catheter 12 generates an electric field. The non-excited patch electrodes 38 may then measure potentials that can be used to determine the position of sensor 32. Accordingly, in such an embodiment, the excitation of multiple electrode pairs comprising different patch electrodes 38 and the catheter-mounted electrode may be used to determine the position of sensor 32.

Data sets from each of patch electrodes 38 and the sensor 32 are all used to determine the location of sensor 32 within heart 20. After the voltage measurements are made, a different pair of patch electrodes 38 is excited by the current source and the voltage measurement process of the remaining patch electrodes 38 and sensor 32 takes place. Once the location of sensor 32 is determined, and as was described above, the location may be recorded as a data point 46 in the same manner described above. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Accordingly, it will be appreciated that any number of techniques may be used to determine locations of sensor 32 and to, therefore, collect data points corresponding thereto, each of which remains within the spirit and scope of the present disclosure.

Figure 3:
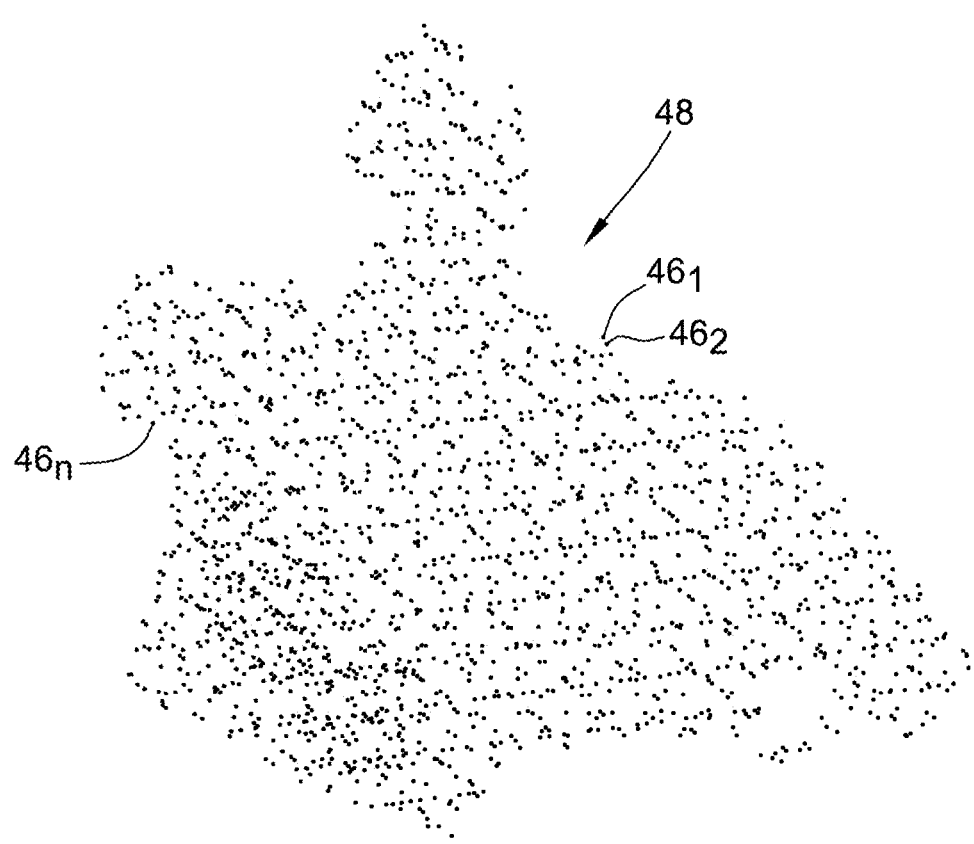
FIG. 3 is a schematic view of a point cloud containing a collection of location data points.
Figure 4A:
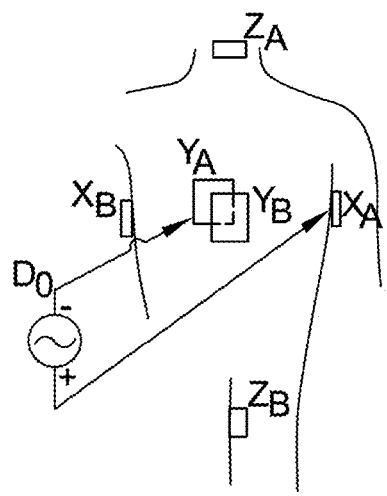
FIGS. 4A-4D are schematic diagrams of exemplary dipole pairs of driven patch electrodes suitable for use in the model construction system illustrated in FIG. 2.
Figure 4B:
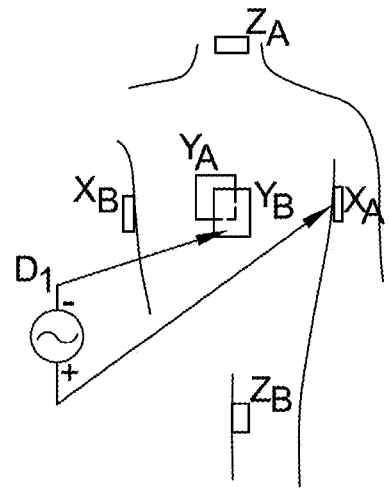
Figure 4C:
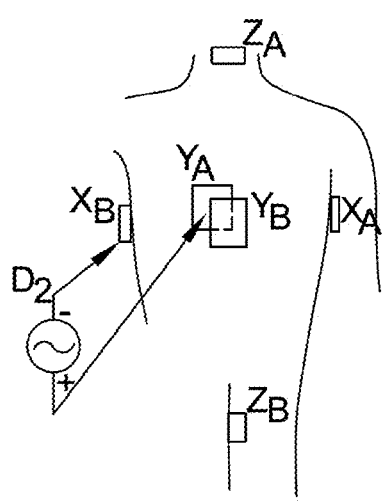
Figure 4D:
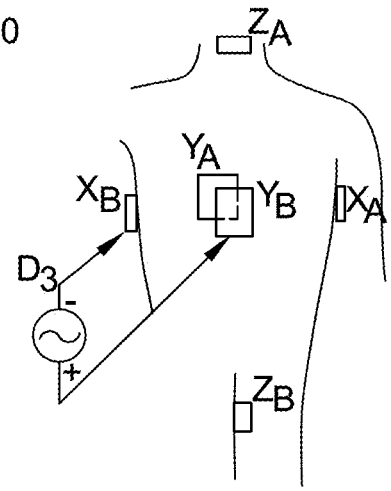

FIG. 3 is illustrative of the point cloud 48 including location data points $46_1$, $46_2$, . . . $46_n$ corresponding to a particular structure of interest being modeled. It will be appreciated that in practice, the point cloud 48 would generally include hundreds to hundreds of thousands of data points 46. For purposes of illustration and ease of description, however, the description below will be limited to a point cloud having a limited number of location data points, such as, for example, point cloud 48 including location data points 46.

As will be appreciated by those skilled in the art, using location data points 46, a geometric surface model of the structure of interest may be generated. Further, diagnostic landmark (DxL) points may also be collected. The DxL points may be, for example, map points at which electrical information (e.g., conductivity, peak voltage, phase information on when a heartbeat reaches that point, etc.) is measured (e.g., using system 10 (shown in FIG. 1)). Notably, the DxL points are generally not co-located with location data points 46 as they are not geometry points, but are points at which electrical information is acquired.

Figure 5:
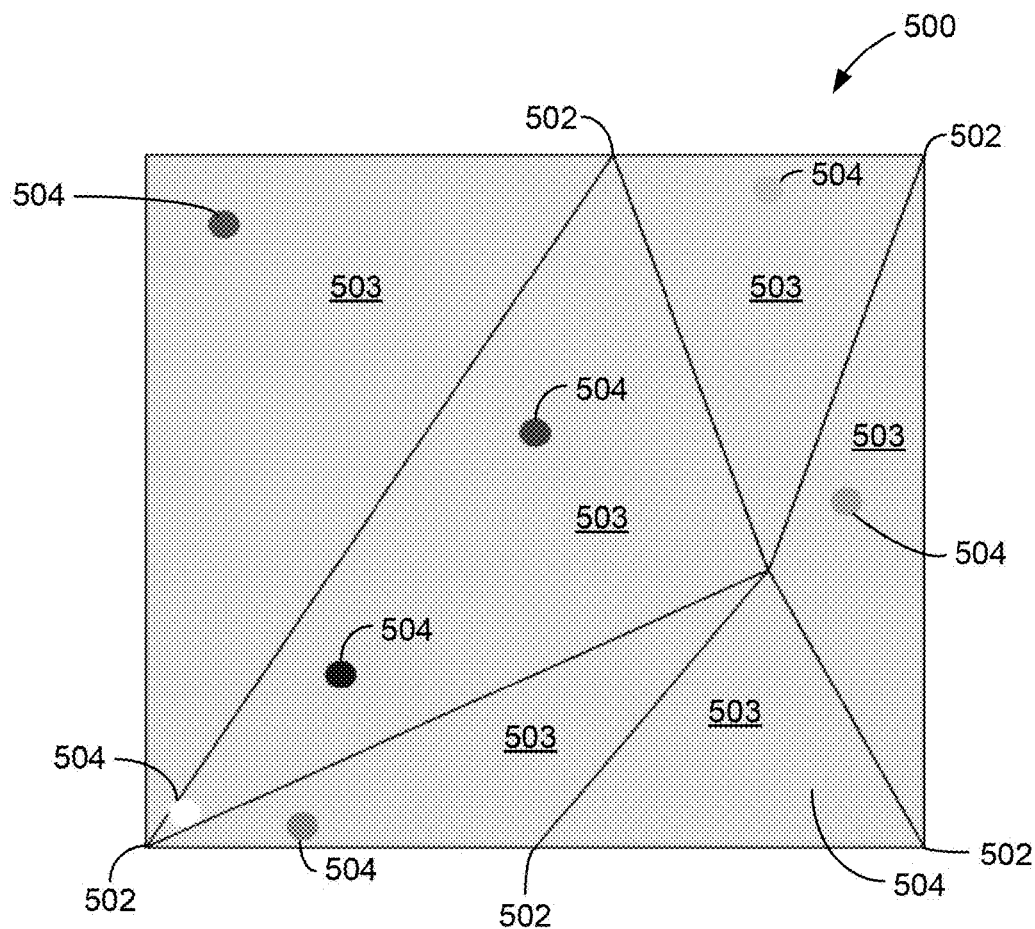
FIG. 5 is an example of an unshaded electrophysiological map acquired using the system illustrated in FIG. 2.

FIG. 5 is an example unshaded electrophysiological map 500 acquired using a system for generating a surface model, such as system 10 (shown in FIG. 1). As shown in FIG. 5, unshaded electrophysiological map 500 includes a plurality of geometric vertices 502. To generate a surface, geometric vertices 502 are connected using triangulation to generate a plurality of facets 503. Unshaded electrophysiological map 500 also includes a plurality of DxL points 504. The color of each DxL point 504 corresponds to the value of the electrical information measured at that point (i.e., the value of a physiological metric, or color value). To generate a final electrophysiological map, color is applied to shade the generated surface to represent the values at DxL points 504.

Figure 6:
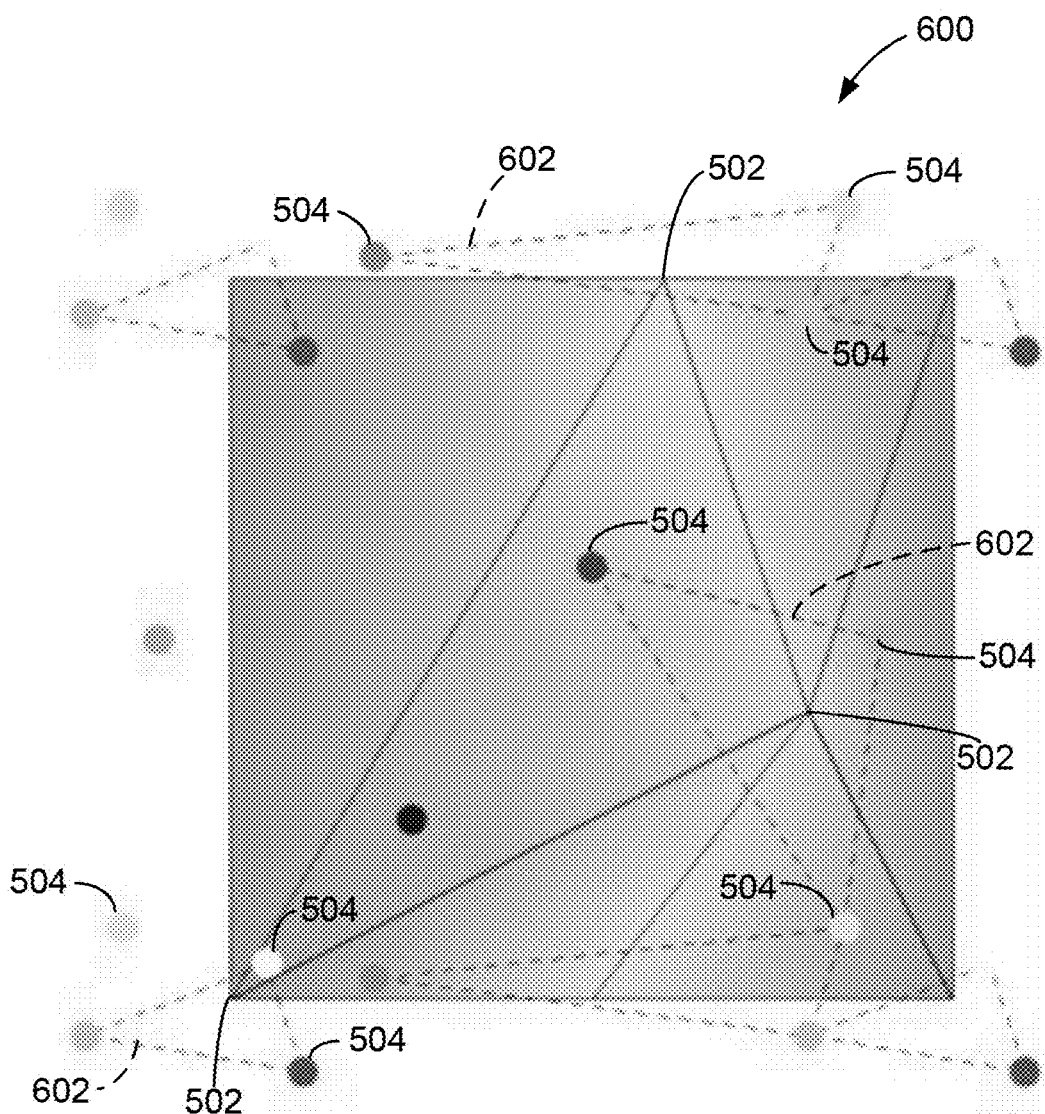
FIG. 6 is an example of a shaded electrophysiological map generated using a known algorithm.

Notably, in at least some known systems, color is applied to unshaded electrophysiological map 500 based on the geometry of geometric vertices 502. For example, FIG. 6 shows an example shaded electrophysiological map 600 generated using a known algorithm. Specifically, to generate shaded electrophysiological map 600, each geometric vertex 502 is colored based on a weighted average of the color values of three nearby DxL points 504 forming a triangle 602. The colors of adjacent geometric vertices 502 are blended together to fill in the intervening space. However, as shown in FIG. 6, this may result in a relatively smeared spectrum for shaded electrophysiological map 600, in which the colors (i.e., corresponding to physiological values) of the DxL points 504 are poorly represented.

Accordingly, in the embodiments described herein, a shaded electrophysiological map is generated using a relatively simple kernel-evaluation loop that fills a relatively large three-dimensional texture map, normalizes physiological metrics, and renders the shaded electrophysiological map directly or indirectly from the three-dimensional texture map, as described herein. This prevents interpolation problems, allows much more electrophysiological detail to be mapped even with geometries including large facets, and runs more quickly that at least some known algorithms.

Figure 7:
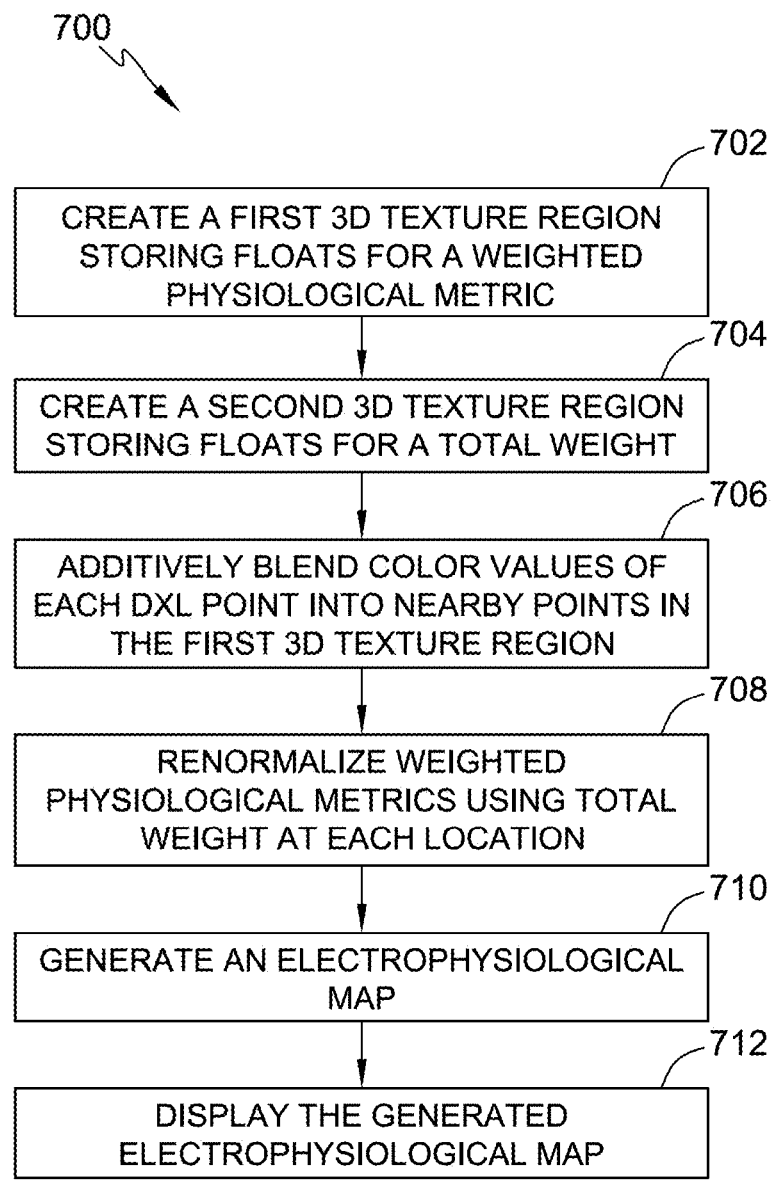
FIG. 7 is a flowchart of a method for generating an electrophysiological map according to one embodiment.

FIG. 7 is a flowchart of one embodiment of a method 700 for generating an electrophysiological map. In the example embodiment, in steps 702 and 704, two relatively large scalar three-dimensional texture regions are created. These 3D texture regions are lattices of voxels or points arranged at regular intervals. A first 3D texture region stores floats for a weighted physiological metric (e.g., peak voltage, conductivity, or phase information, used as a color index to determine the displayed color from a spectrum or otherwise used to determine the displayed color), and the second 3D texture region stores floats for a total weight. The 3D texture regions are large enough to include the entire geometry model (e.g., the entire unshaded electrophysiological map 500). In one embodiment, the 3D texture regions have an 0.5 millimeter (mm) resolution over their entire volume. Further, in some embodiments, the first and second 3D texture maps are generated by generating a single 3D texture region that stores floats for both the weighted physiological metric and the total weight.

At step 706, for each DxL point 504, the physiological value of the DxL point 504 is additively blended into nearby points (i.e., voxels) in the first 3D texture region according to a weighting function. Specifically, for each voxel in the first 3D texture region that is within a predetermined distance of particular DxL point 504, a weight is computed, the voxel's total weight is incremented by that computed weight, and the voxel's weighted average map data is incremented by the product of that weight with the physiological metric associated with that DxL point 504. Each voxel stores a weighted average of all DxL points 504 within the predetermined distance, according to methods that will be understood by those of skill in the art. The predetermined distance may be determined, for example, by a setting of an interpolation slider. If the range of the map's color spectrum is [0, 1], the resulting physiological metric values are in [0, w(x)] at each location x, where w(x) is the value of the total weight texture (i.e., the second 3D texture region) value at that location.

The computed weight may be a function of the distance from that voxel to the DxL point 504. For example, the weight may be a function of a quantity kr, where r is a distance (e.g., in mm) from DxL point 504 to the voxel. In some embodiments, k is a predetermined constant. In other embodiments, k may be variable (e.g., k may be region specific or vary for each DxL point 504). For example, for a given DxL point 504, k may be half the distance to the nearest neighboring DxL point 504. The function could be, for example, $1/(1+k^2r^2)$, $1/(1+k^4r^4)$, or $(1/(1+k^2r^2))^2$. Further, splines that blend to zero could also be used, such as $\{1-3k^2r^2+2k^3r^3$ for r in $[0, 1/k]$; 0 otherwise$\}$ or $\{(1-k^2r^2)^3$ for r in $[0, 1/k]$; 0 otherwise$\}$. Notably, this ties the predetermined distance to a half-width, $1/k$, of the weighting function.

Using this computation of the weight, nearby DxL points 504 will blend into each other, but will not obscure each other, unless they are very close relative to the half-width of the weighting function (e.g., less than 0.5 mm). In some embodiments, the half-width is chosen individually for each DxL point 504 (e.g., half the distance to a nearest neighbor DxL point 504).

Additively blending each DxL point 504 into nearby points in the first 3D texture region can be intuitively illustrated as "paintballing" the DxL points 504 into the first 3D texture region. Specifically, "paintballing" the physiological metric onto voxels or points in the first 3D texture region may be thought of as effectively using paintballs that have different concentrations of dye, but with each paintball having the same size (i.e., such that each has the same amount of liquid with different amounts of dye). Each voxel or point in the first 3D texture region may then be thought of as a vial that collects whatever paint lands on it. After "paintballing" all of the DxL points 504, each voxel or point may have accumulated different amounts of "liquid" from several "paintballs". That is, some voxels or points may be "painted" more thickly. Accordingly, the amount of "paint" is normalized based on the total amount of "paint" delivered to each voxel (i.e., by dividing the un-normalized physiological metric by the total weight). In this embodiment, this normalized physiological metric is used to look up a corresponding color to be displayed.

Figure 8:
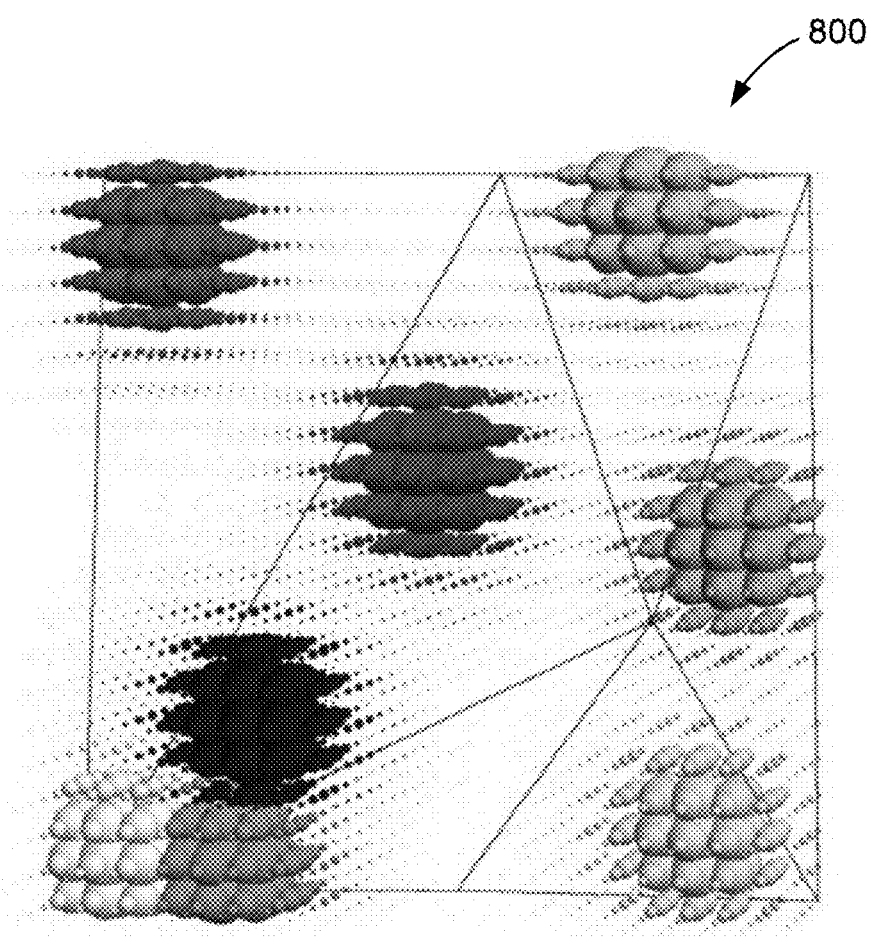
FIG. 8 is a diagram illustrating the result of one of the steps of the method illustrated in FIG. 7.

FIG. 8 is a diagram 800 illustrating the result of step 706 in one embodiment. As shown in FIG. 8, lattice points neighboring each DxL point 504 are colored based on the physiological value of the nearest DxL point 504 and their respective distances from the nearest DxL point 504.

At step 708, the weighted physiological metrics (i.e., the un-normalized physiological metrics) are renormalized into [0,1] using the total weight at each location. That is, at step 708, the "paintballed" first 3D texture map is divided by the second 3D texture map to create a weighted average color. This allows regions close to only one DxL point 504 to have a constant color, and also facilitates guaranteeing that all DxL points 504 will affect the final map, even if there are multiple DxL points 504 in the same facet 503, and regardless of facet size.

To generate the electrophysiological map, at step 710, triangles of the geometry model are drawn using each geometric vertex 502 as an index into the normalized 3D texture map. That is, geometry vertices 502 are used as the texture coordinates to get the correct physiological metric into the current map-color spectrum. In some embodiments, the physiological metric is used as the s texture coordinate and the distance from each geometry vertex 502 to the nearest DxL point 504 is used as the t texture coordinate in a two-dimensional (s, t) texture space to generate an electrophysiological map with relatively well-defined round edges. That is, the normalized map data at each geometry vertex 502 may be used as an index into a separate one-dimensional texture map of color, or a two-dimensional texture map whose other index is distance.

To facilitate improving rendering speed, for step 706, in some embodiments, the additive blending can be applied in a relatively thin two-dimensional region surrounding the geometry model, instead of in full 3D. In another embodiment, the geometry could first be rendered into an empty 3D texture map to create a bitfield of texture voxels that intersect the surface model, since those are the only texture points that need to be colored. In yet another embodiment, to increase the rendering speed, the actual 3D weighting texture may be used as the bitfield after initializing it to −1.0, and rendering to set voxels intersecting the surface to an initial weight of 0.0.

Figure 9:
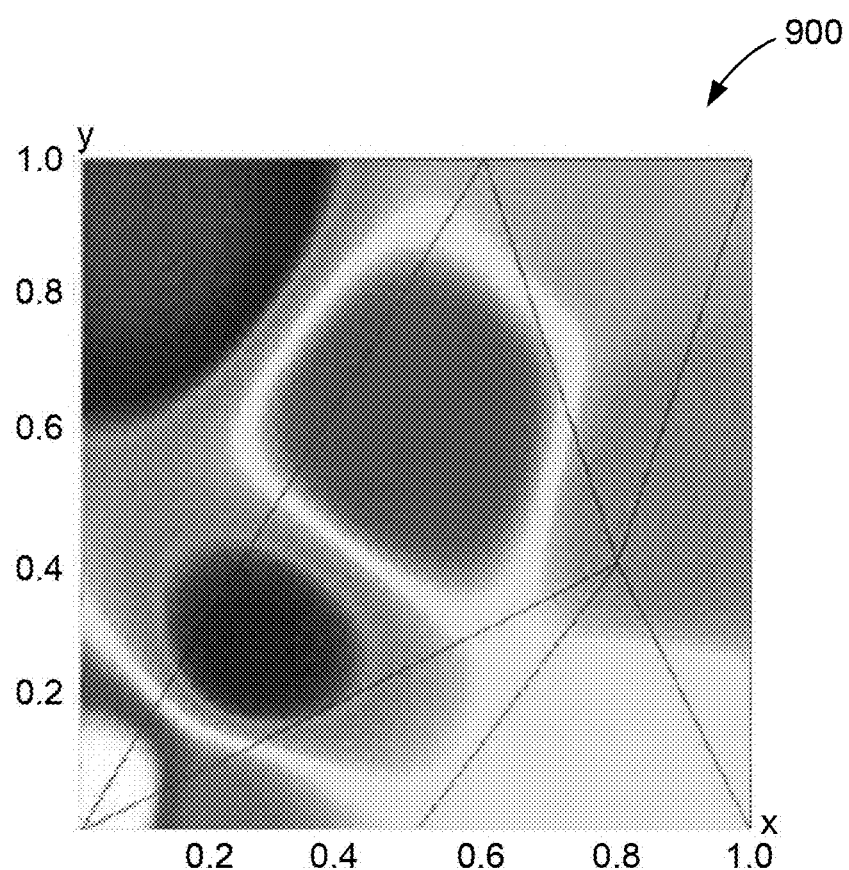
FIG. 9 is an example of a shaded electrophysiological map generated using the method illustrated in FIG. 7.

At step 712, the generated electrophysiological map is displayed to a user (e.g., on display 44 (shown in FIG. 2)). FIG. 9 is an example shaded electrophysiological map 900 generated using method 700. Notably, map 900 and map 600 are both generated from map 500. Map 600 is generated using known methods, and map 900 is generated using the systems and methods described herein. Compared to map 600, however, map 900 represents the colors of DxL points 504 much more accurately. Further, unlike map 600, map 900 does not include a smeared color palette.

It should be understood that model construction system 14, and particularly processing apparatus 16, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for generating an electrophysiological map of a geometric structure, the system comprising:
a computer-based model construction system configured to be coupled to a device that includes at least one sensor configured to acquire a set of original location data points corresponding to respective locations on a surface of the geometric structure, the computer-based model construction system further configured to:
generate a geometric surface model of the geometric structure based on the set of original location data points;
acquire electrical information at a plurality of diagnostic landmark points;
assign a color value, based on the acquired electrical information, to each of the diagnostic landmark points;
create a first three-dimensional (3D) texture region storing floats for a weighted physiological metric;
create a second 3D texture region storing floats for a total weight;
for each diagnostic landmark point, additively blend the color value of the diagnostic landmark point into voxels of the first 3D texture region that are within a predetermined distance from the diagnostic landmark point;
normalize the colored voxels using the second 3D texture region to generate a normalized 3D texture map;
apply the normalized 3D texture map to the geometric surface model to produce the electrophysiological map; and
display the electrophysiological map.

2. The system of claim 1, wherein to additively blend the color value of the diagnostic landmark point into voxels of the first 3D texture region, the computer-based model construction system is configured to additively blend the color value of the diagnostic landmark point into voxels of the first 3D texture region across a 3D volume.

3. The system of claim 1, wherein to additively blend the color value of the diagnostic landmark point into voxels of the first 3D texture region, the computer-based model construction system is configured to additively blend the color value of the diagnostic landmark point into voxels of the first 3D texture region across a 2D area of the geometric surface model.

4. The system of claim 1, wherein to additively blend the color value of the diagnostic landmark point into voxels of the first 3D texture region, the computer-based model construction system is configured to, for each voxel within the predetermined distance:
compute a weight for the voxel;
increment the voxel's total weight; and
increment the weighted average map data for the voxel.

5. The system of claim 1, wherein to additively blend the color value of the diagnostic landmark point into voxels of the first 3D texture region, the computer-based model construction system is configured to additively blend the color value of the diagnostic landmark point into voxels using a weighting function that is dependent on k and r, wherein k is one of a variable and a constant, and wherein r is a distance between a voxel and the diagnostic landmark point.

6. The system of claim 5, wherein the weighting function is $1/(1+k^2r^2)$, $1/(1+k^4r^4)$, or $(1/(1+k^2r^2))^2$.

7. The system of claim 5, wherein k is half of a distance from the diagnostic landmark point to a nearest diagnostic landmark point.

8. The system of claim 1, wherein to create a first 3D texture region and a second 3D texture region, the computer-based model construction system is configured to generate a single 3D texture region that includes floats for both the weighted physiological metric and the total weight.

9. A computer-implemented method of generating an electrophysiological map of a geometric structure, the method comprising:
receiving a set of original location data points corresponding to respective locations on a surface of the geometric structure;
generating a geometric surface model of the geometric structure based on the received original location data points;
acquiring electrical information at a plurality of diagnostic landmark points;
assigning a color value, based on the acquired electrical information, to each of the diagnostic landmark points;
creating a first three-dimensional (3D) texture region storing floats for a weighted physiological metric;
creating a second 3D texture region storing floats for a total weight;
for each diagnostic landmark point, additively blending the color value of the diagnostic landmark point into voxels of the first 3D texture region that are within a predetermined distance from the diagnostic landmark point;
normalizing the colored voxels using the second 3D texture region to generate a normalized 3D texture map;
applying the normalized 3D texture map to the geometric surface model to produce the electrophysiological map; and
displaying the electrophysiological map.

10. The method of claim 9, wherein additively blending the color value of the diagnostic landmark point into voxels of the first 3D texture region comprises additively blending the color value of the diagnostic landmark point into voxels of the first 3D texture region across a 3D volume.

11. The method of claim 9, wherein additively blending the color value of the diagnostic landmark point into voxels of the first 3D texture region comprises additively blending the color value of the diagnostic landmark point into voxels of the first 3D texture region across a 2D area of the geometric surface model.

12. The method of claim 9, wherein additively blending the color value of the diagnostic landmark point into voxels of the first 3D texture region comprises, for each voxel within the predetermined distance:
computing a weight for the voxel;
incrementing the voxel's total weight; and
incrementing the weighted average map data for the voxel.

13. The method of claim 9, wherein additively blending the color value of the diagnostic landmark point into voxels of the first 3D texture region comprises additively blending the color value of the diagnostic landmark point into voxels using a weighting function that is dependent on k and r, wherein k is one of a variable and a constant, and wherein r is a distance between a voxel and the diagnostic landmark point.

14. The method of claim 13, wherein the weighting function is $1/(1+k^2r^2)$, $1/(1+k^4r^4)$, or $(1/(1+k^2r^2))^2$.

15. The method of claim 13, wherein k is half of a distance from the diagnostic landmark point to a nearest diagnostic landmark point.

16. The method of claim 9, wherein creating a first 3D texture region and a second 3D texture region comprises generating a single 3D texture region that includes floats for both the weighted physiological metric and the total weight.

17. A processing apparatus for generating an electrophysiological map of a geometric structure, the processing apparatus configured to:
receive a set of original location data points corresponding to respective locations on a surface of the geometric structure;
generate a geometric surface model of the geometric structure based on the received original location data points;
acquire electrical information at a plurality of diagnostic landmark points;
assign a color value, based on the acquired electrical information, to each of the diagnostic landmark points;
create a first three-dimensional (3D) texture region storing floats for a weighted physiological metric;
create a second 3D texture region storing floats for a total weight;
for each diagnostic landmark point, additively blend the color value of the diagnostic landmark point into voxels of the first 3D texture region that are within a predetermined distance from the diagnostic landmark point;
normalize the colored voxels using the second 3D texture region to generate a normalized 3D texture map;
apply the normalized 3D texture map to the geometric surface model to produce the electrophysiological map; and
display the electrophysiological map.

18. The processing apparatus of claim 17, wherein to additively blend the color value of the diagnostic landmark point into voxels of the first 3D texture region, the processing apparatus is configured to additively blend the color value of the diagnostic landmark point into voxels of the first 3D texture region across a 3D volume.

19. The processing apparatus of claim 17, wherein to additively blend the color value of the diagnostic landmark point into voxels of the first 3D texture region, the processing apparatus is configured to additively blend the color value of the diagnostic landmark point into voxels of the first 3D texture region across a 2D area.

20. The processing apparatus of claim 17, wherein to additively blend the color value of the diagnostic landmark point into voxels of the first 3D texture region, the processing apparatus is configured to, for each voxel within the predetermined distance:
  compute a weight for the voxel;
  increment the voxel's total weight; and
  increment the weighted average map data for the voxel.

* * * * *